US011541408B2

(12) United States Patent
Cohen et al.

(10) Patent No.: US 11,541,408 B2
(45) Date of Patent: Jan. 3, 2023

(54) HAIR TREATMENT SYSTEM, TREATMENTS AND APPARATUS

(71) Applicant: 2B1K IMPORTS PTY LTD, Bondi Junction (AU)

(72) Inventors: Ben Jan Cohen, Bondi Junction (AU); Benny Risher, Bondi Junction (AU); Noah Roet, Picton (AU); Samir Maarbani, Mount Druit (AU)

(73) Assignee: 2B1K Imports PTY LTD, Bondi Junction (AU)

( * ) Notice: Subject to any disclaimer, the term of this patent is extended or adjusted under 35 U.S.C. 154(b) by 830 days.

(21) Appl. No.: 16/479,277

(22) PCT Filed: Jan. 20, 2017

(86) PCT No.: PCT/AU2017/050047
§ 371 (c)(1),
(2) Date: Jul. 19, 2019

(87) PCT Pub. No.: WO2017/124154
PCT Pub. Date: Jul. 27, 2017

(65) Prior Publication Data
US 2019/0381527 A1    Dec. 19, 2019

(30) Foreign Application Priority Data

Jan. 21, 2016 (AU) ................................. 2016900183

(51) Int. Cl.
*B05B 7/24* (2006.01)
*B05B 1/18* (2006.01)
(Continued)

(52) U.S. Cl.
CPC ............ *B05B 7/2462* (2013.01); *A61K 8/022* (2013.01); *A61Q 5/02* (2013.01); *A61Q 5/12* (2013.01);
(Continued)

(58) Field of Classification Search
CPC ......... B05B 7/2462; B05B 1/18; B05B 1/185; B01F 1/0033
See application file for complete search history.

(56) References Cited

U.S. PATENT DOCUMENTS 1,751,524 A * 3/1930 Moss ..................... E03C 1/046
239/315
3,008,650 A * 11/1961 Prokop, Sr. ............... B05B 1/18
239/596
(Continued)

FOREIGN PATENT DOCUMENTS

EP          2351888 A1 *  8/2011  ............ E03C 1/046
FR          2981284        4/2013
(Continued)

OTHER PUBLICATIONS

International Search Report for PCT/AU2017/050047 dated Apr. 3, 2017, 5 pgs.
(Continued)

*Primary Examiner* — Joseph A Greenlund
(74) *Attorney, Agent, or Firm* — Lowenstein Sandler LLP (57) ABSTRACT

A hand held shower head configured to deliver a continuous dose of water dispersed treatment from a water disintegratable treatment source, the shower head including: a hollow body having water inlet opening and water outlet, the water outlet defined by a perforated plate, and a mesh formation disposed within the hollow body between the water inlet opening and the perforated plate, wherein the water inlet opening, hollow body and perforated plate are configured to create in use a pressurised turbulent water flow within the hollow body prior to exiting through the perforated plate, whereby a water disintegratable tablet treatment source introduced into the hollow body prior to use, is then agitated by the turbulent water flow against the mesh in an abrading manner and thereby dispersed into the water flow exiting the (Continued)

perforated plate. A water disintegratable tablet comprising emulsifier, thickening agent, surfactants, oil and rheology modifier is also disclosed.

8 Claims, 4 Drawing Sheets

(51) Int. Cl.
| | | |
|---|---|---|
| E03C 1/046 | (2006.01) | |
| C02F 1/00 | (2006.01) | |
| A61K 8/02 | (2006.01) | |
| A61Q 5/02 | (2006.01) | |
| A61Q 5/12 | (2006.01) | |
| B05B 1/34 | (2006.01) | |
| C02F 1/68 | (2006.01) | |
| B01F 21/20 | (2022.01) | |
| B01F 25/452 | (2022.01) | |
| B01F 21/00 | (2022.01) | |
| B01F 101/48 | (2022.01) | |

(52) U.S. Cl.
CPC ........ *B01F 21/221* (2022.01); *B01F 25/4521* (2022.01); *B01F 25/45241* (2022.01); *B05B 1/18* (2013.01); *B05B 1/3426* (2013.01); *C02F 1/003* (2013.01); *C02F 1/688* (2013.01); *E03C 1/046* (2013.01); *B01F 21/503* (2022.01); *B01F 2101/48* (2022.01); *B05B 1/34* (2013.01); *B05B 1/341* (2013.01); *C02F 2307/06* (2013.01)

(56) References Cited

U.S. PATENT DOCUMENTS

| | | | | |
|---|---|---|---|---|
| 3,120,015 A * | 2/1964 | MacChesney | ........ | B05B 7/2462 239/266 |
| 3,921,635 A * | 11/1975 | Gauthier | ............... | A61M 3/025 4/615 |
| 4,211,368 A * | 7/1980 | Legros | .................. | B05B 7/2443 239/315 |
| 5,957,387 A * | 9/1999 | Porta | ...................... | E03C 1/046 239/315 |
| 6,006,374 A * | 12/1999 | Winnett | .................. | E03C 1/046 4/525 |
| 6,395,172 B1 * | 5/2002 | Koike | ..................... | C02F 1/688 210/502.1 |
| 7,866,572 B2 * | 1/2011 | Ichige | .................. | B05B 7/0425 239/419 |
| 2009/0090793 A1 * | 4/2009 | Ichige | ..................... | E03C 1/084 239/428.5 |
| 2009/0101733 A1 * | 4/2009 | Popov | .................. | B05B 1/1636 4/615 |
| 2011/0290913 A1 * | 12/2011 | Jung | ..................... | B05B 7/2462 239/310 |
| 2018/0355591 A1 * | 12/2018 | Saro | ........................ | E03C 1/0409 |
| 2019/0381527 A1 * | 12/2019 | Cohen | ...................... | A61Q 5/02 |

FOREIGN PATENT DOCUMENTS

| | | | |
|---|---|---|---|
| JP | S6339653 A | | 2/1998 |
| JP | 3165747 U | | 5/2001 |
| JP | 2002282156 A | | 10/2002 |
| JP | 2003265351 A | | 9/2003 |
| JP | 2014050543 | | 3/2014 |
| JP | 2014050543 A | * | 3/2014 |
| JP | 2014083411 A | | 5/2014 |
| JP | 2016087599 A | | 5/2016 |
| JP | 2017012644 A | | 1/2017 |
| KR | 20130019047 A | * | 2/2013 |

OTHER PUBLICATIONS

European Search Report for EP17740917 dated Jul. 27, 2020, 2 pages.
International Search Report for EP17740917 dated Jul. 27, 2020, 42 pages.
English Translation of Office Action for JP2019540005 dated Feb. 1, 2021, 9 pages.

* cited by examiner

_FIG 8(a)_  _FIG 8(b)_

_FIG 9_

HAIR TREATMENT SYSTEM, TREATMENTS AND APPARATUS

CROSS-REFERENCE TO RELATED APPLICATION(S)

This application is a national phase entry under 35 U.S.C. § 371 of International Application No. PCT/AU2017/050047, filed on Jan. 20, 2017. The content of the application is hereby incorporated by reference herein in its entirety.

FIELD OF THE INVENTION

The present invention relates to hair treatment system including a treatment application apparatus, a range of hair treatments and an associated hair treatment process and regime.

The invention has been developed primarily for use by hair care professionals in a salon environment, but is not limited to this particular field of use.

BACKGROUND OF THE INVENTION

Any discussion of the prior art throughout the specification should in no way be considered as an admission that such prior art is widely known or forms part of common general knowledge in the field.

The majority of hair treatment processes to date have been based on a discontinuous process of first wetting the hair, separately applying a cleanser or treatment product to the wet or dampened hair, rinsing, and then applying a further treatment as required.

While there are systems available that offer means of applying some form of water conveyed conditioner or cleanser product during the hair wetting process, these have limitations. For example products that automatically deliver liquid cleansers into fixed bathroom shower heads do not provide any dosage control and cannot be directed in a controlled manner to different regions of the hair and scalp.

Similarly, the professional systems that propose use of solid tablets of cleanser or water conditioner in a hand held shower head, have one or more problems including: difficulty achieving a controlled rate of delivery of the cleanser; blocking the holes or perforations in the outlet plate; or needing to use and subsequently remove special containers that deliberately inhibit normal water flow conditions to reduce the rate of dissolution of the tablet. In many cases users of the latter system choose to simply dissolve the tablets in water in the basin and then soak the client's hair in the resulting solution.

It is an object of the present invention to overcome or ameliorate the above discussed disadvantages of the prior art, or at least offer a useful alternative.

SUMMARY OF THE INVENTION

Shower Head Apparatus

According to a first aspect the present invention provides a hand held shower head configured to deliver a continuous dose of water dispersed treatment from a water disintegratable tablet form treatment source, the shower head including:

a hollow body having a water inlet opening at one region and a water outlet at another region, the water outlet being defined by a perforated plate, and a fixed mesh formation disposed between the water inlet opening and the perforated plate, wherein the water inlet opening, hollow body and perforated plate are configured to create in use a pressurised turbulent water flow within the hollow body prior to exiting through the perforated plate, whereby a suitably configured water disintegratable solid tablet form treatment source introduced into the hollow body intermediate the mesh and the water inlet opening prior to use, is then agitated by the turbulent water flow against the mesh formation in an abrading manner and thereby dispersed into the water flow exiting the perforated plate.

By "water distintegratable" is meant that the tablet will disintegrate when exposed to a flow of water over a period of time. It would be understood that components of the tablet may be soluble in water, though it is not essential that all components be water soluble for the tablet to disintegrate when exposed to a flow of water.

The term "mesh" is used herein to refer to any rigid perforate structure that defines a matrix of rigid elements against which the tablet can abrade, while at the same time not substantially obstructing water flow within the hollow body and through the perforated plate. It is not intended to be limited to woven formations.

Preferably the fixed mesh formation is disposed adjacent, but spaced slightly from, the perforated plate. Desirably, the water inlet opening is configured to deliver water into the hollow body in a plane which is generally parallel to and spaced from the perforated plate, and the hollow body is shaped to direct at least a portion of that water flow from the inlet downwardly toward the plate to thereby create a turbulent water flow within the body.

Desirably, the internal shape of the body is configured such that a rotating water flow path is created which at least in part circles within the body tangentially to the plate.

In this manner a generally circulating turbulent flow is created which entrains the solid treatment tablet causing it to rotate or otherwise move within the turbulent flow and repeatedly abrade against the mesh formation which assists with the disintegration process.

Preferably the mesh is configured to provide minimum disruption to normal flow within the hollow body and through the perforated plate.

More preferably the mesh is configured to define a bowl like cradle portion opening away from the perforated plate. Preferably the mesh formation extends across the full area of the perforated plate accessible by the water from within the hollow body. Ideally the cradle also has outwardly sloping sides. This cradle shape acts to locate an appropriately sized and shaped treatment tablet when it is first inserted within the shower head and as it moves toward the perforated plate, and the sloping sides act to help deflect the slowly disintegrating tablet that is forced toward the mesh by the water flow, back into the turbulent flow region and/or a central portion of the hollow body.

Desirably, the shower head also includes means to aerate the water flow. In one preferred form this is achieved by provision of aeration pre-treatment chamber disposed upstream of the inlet to the hollow body. In one embodiment, the aeration is achieved by captively locating particulate matter in the pre-treatment chamber, whereby passage of water through this chamber around the particulate matter causes air bubbles of air to be created which pass through with the water into the hollow body Air may also be entrained into the hollow body through the perforated plate, which is preferably slightly concave when viewed from outside the device.

Preferably, the particulate matter is in bead form. More preferably, the particulate matter comprises a material that also interacts with the water to enhance its properties by, for example, ionising the water. Suitable bead materials include Tourmaline, Silver, Cerussite, Vitamin C, Vitamin D and products such as Million Guard™ produced by Koa Glass Company and which is an antimicrobial glass powder with Silver ions retained in the glass network structure that are gradually released. Desirably the shower head is configured such that in use the water is entering the hollow body from an upper region thereby creating a waterfall-like stream which in turn enhances the Lenard effect by colliding with the lower wetted surfaces in the hollow body to produce negative ions. Such ions may already be present as the water collides with the wetted particulate matter in the pre-treatment chamber, where this is included.

Preferably the shower head also includes means for filtering out unwanted impurities such as chlorine or the like. This may be part of, or separate to, the means for generating negative ions.

Preferably, the shower head and disintegratable tablets are configured such that during use with a warm water supply at typical pressure and hair washing temperature, the tablets take around 2 to 4 minutes to disintegrate and provide a flow of water dispersed treatment to a user. Examples of typical water inlet pressure to the shower heads include a pressure range of 50-200 KPa, temperature range of 10-40 degrees Celsius and outlet flow rate of 4-12 litres per minute, preferably 5-8 litres per minute as may be controlled by a flow regulator.

Desirably, the shower head is configured as an increased pressure reduced water usage shower head.

In one preferred form, the increased pressure and reduced water usage is achieved at least in part by use of a perforated plate having a thickness range of 0.2 to 0.35 millimetres and perforations of a preferably round shape, 0.02 to 0.03 millimetres in diameter, with a total of between approximately 300 and 500 perforations and more preferably about 400 perforations. Preferably, the pattern of perforations is arranged to be concentrated around a central region of the perforated plate and do not extend to the circumferentially outer portion of the plate to provide a focused spray pattern whereby the water (with or without treatment) can be carefully directed to regions of the head undergoing treatment and reduce the risk of the spray extending beyond the treatment basin. Preferably the inlet to the hollow body is small so as to increase the pressure of the water entering the hollow body. In one preferred form the inlet is in the form of a slit opening with a maximum length of around 10-14 mm and maximum width of about 2-3 mm. The shower head includes means to enable a resealable access to the hollow body to insert the treatment tablet. In one form the access is provided by removing the portion of the shower head housing the perforated plate, which is preferably secured by a quick release mechanism such as a bayonet style fitting.

In another embodiment access is provided a small resealable opening into the hollow body.

While the preferred forms of the invention include a fixed mesh within the hollow body, in another form the mesh may be designed to encapsulate the tablet in a similar manner to a tea strainer pod, whereby the entire mesh pod moves within the turbulent flow, and the tablet moves within the mesh pod in an abrading manner and is thereby dispersed into the water flow exiting the perforated plate.

Hair Treatments

According to a second aspect, the present invention provides a water distintegratable tablet comprising an emulsifier, a thickening agent, an oil and a rheology modifier.

By "water distintegratable" is meant that the tablet will disintegrate when exposed to a flow of water over a period of time. It would be understood that components of the tablet may be soluble in water, though it is not essential that all components be water soluble for the tablet to disintegrate when exposed to a flow of water. The tablet may be a solid, waxy tablet.

In embodiments of the invention, the tablet is used for cosmetic purposes, which may include hair treatments.

The rheology modifier used in the tablets of the present invention may be any compound or composition suitable for increasing the viscosity of the fluid components of the tablets during manufacture. The rheology modifier may increase the viscosity of the fluid components by stabilising oil-in-water and water-in-oil emulsions to aid in the formation of the tablets. By "suitable" is meant that the components in the resulting viscous mixture of components are relatively evenly dispersed, remain active and are resistant to degradation or disintegration (when not exposed to water) over time. The skilled addressee would understand that a rheology modifier is essentially a compound that, when added to mixtures of fluid components or emulsions with low viscosity may increase the viscosity of the mixture of fluid components or emulsion, or at least maintain the viscosity of the emulsion, and generally assist in the maintenance of stable emulsions.

The rheology modifier may comprise inorganic or organic molecules and may generally be added to the mixture of fluid components or emulsion as an aqueous phase. It is preferably an organic molecule, such as an organic polymer. Organic molecules suitable for use in the present invention as rheology modifiers include, but are not limited to, polyacrylates, polyurethanes and polyethers.

In preferred embodiments of the invention, the tablets comprise an organic polymer that is water soluble.

The rheology modifier may also be co-polymer. The skilled addressee would understand that a co-polymer is any polymer comprising more than one type of monomer.

The percentage of each monomer in the co-polymer, as well as the length of any organic polymer for use in the tablets of the present invention, will be dependent on the desired properties of the rheology modifier. It would be understood by the person skilled in the art that the desired properties of the rheology modifier may also be influenced by the properties of other components in the tablets: for example, whether the tablets comprised a UVR filtering agent that was a solid or liquid, and/or whether the protein extracts was oil, water or solvent soluble or miscible, may influence the choice of rheology modifier. Further to this, the total oil content in the tablets may also influence the choice of rheology modifier. The choice of rheology modifier may also be influenced by the required dissolution rate of the particular tablets.

In preferred embodiments of the invention, the rheology modifier is a water-soluble organic polymer selected from the group consisting of carbomers and polyethylene glycols.

In preferred embodiments, the rheology modifier is a polyethylene glycol or a derivative thereof. In particularly preferred embodiments, the rheology modifier is PEG-4000.

In preferred embodiments of the invention, the tablets may comprise the rheology modifier at a concentration of about 5-50% (w/w). More preferably, the tablets may comprise a rheology modifier at a concentration of about 20-50% (w/w). In further preferred embodiments, the tablets may comprise a rheology modifier at a concentration of about 30%-40% (w/w). In other preferred embodiments, the tablets may comprise a rheology modifier at a concentration of about 20%, 25%, 30%, 35%, 40% or 45% (w/w).

In alternative embodiments, the rheology modifier is a glycerine, glycerol ester or a derivative thereof. The glycerol ester may, for example, be glyceryl oleate or glyceryl stearate. It would be understood that the glycerol esters may also behave as anionic emulsifiers.

In particularly preferred embodiments, the tablets of the present invention comprise a polyethylene glycol at a concentration of about 30%-45% (w/w).

In other preferred embodiments of the present invention, the tablets comprise PEG-4000 at a concentration of about 30%, 35%, 40% or 45% (w/w).

In particularly preferred embodiments, the tablets of the present invention comprise a glycerol ester at a concentration of about 10%-20%, 15%-25, 5%-15%, 20%-40%, or 35%-45% (w/w).

In other preferred embodiments of the present invention, the tablets comprise a glycerol ester or a derivative thereof at a concentration of about 5%, 10%, 15%, 20%, 25%, 30%, 35%, 40% or 45% (w/w).

In particularly preferred embodiments, the tablets of the present invention comprise glyceryl stearate or a derivative thereof at a concentration of about 10%-20%, 15%-25, 5%-15%, 20%-40%, or 35%-45% (w/w).

In particularly preferred embodiments, the tablets of the present invention comprise glyceryl oleate or a derivative thereof at a concentration of about 10%-20%, 15%-25, 5%-15%, 20%-40%, or 35%-45% (w/w).

The emulsifier used in the tablets of the present invention may be any compound or composition suitable for producing mixtures of substances that would not ordinarily mix (emulsions). In general, an emulsifier consists of a water-loving hydrophilic head and an oil-loving hydrophobic tail. The emulsifier may be an oil-in-water or water-in-oil emulsifier.

In embodiments of the present invention, the emulsifier may be an ionic (cationic or anionic) emulsifier, a zwitterionic emulsifier or a non-ionic emulsifier.

Non-limiting examples of cationic emulsifiers suitable for use in the tablets of the present invention include quaternary ammonium compounds such as benzalkonium chloride, benzethonium chloride, stearalkonium chloride and cetrimonium chloride.

It would be understood that the cationic emulsifiers may also serve as an antibacterial agent in view of the known ability of cationic surfactants to disrupt the cell membrane of some microorganisms.

Non-limiting examples of anionic emulsifiers suitable for use in the tablets of the present invention include sodium lauryl sulfate (SLS), ammonium lauryl sulfate (ALS), or their ethoxylated companions, sodium laureth sulfate (SLES), sodium docusate, the taurates, the isethionates, the olefin sulfonates, and the sulfosuccinates.

Non-limiting examples of zwitterionic emulsifiers suitable for use in the tablets of the present invention include sodium lauriminodipropionate and Disodium lauroamphodiacetate.

Non-limiting examples of nonionic emulsifiers suitable for use in the tablets of the present invention include sorbitan esters and polyoxyethelene derivatives of sorbitan esters such as the Tweens (polysorbate), long chain (fatty) alcohols such as cetyl alcohol, cetearyl alcohol, lauryl alcohol, oleyl alcohol, stearyl alcohol, polyoxyethylene ethers of fatty alcohols, such as ceteareth, ceteth, oleth, steareth and laureth, the fatty alcohol ethoxylates, fatty alcohol alkoxylates, and nonylphenyl ethoxylates.

The tablets may comprise one or more emulsifiers that is/are a nonionic emulsifier selected from the group consisting of a cetearyl alcohol, a ceteareth, a Tween emulsifier, an alcohol alkoxylate, an alcohol ethoxylate and a nonylphenyl ethoxylate.

In preferred embodiments of the invention, the tablets comprise the non-ionic emulsifier known as Emulagade 1000NI (BASF), which comprises cetearyl alcohol and ceteareth-20.

In preferred embodiments of the invention, the tablets comprise the alcohol alkoxylate known as TERIC BL8 (Huntsman).

In preferred embodiments of the invention, the tablets comprise the alcohol ethoxylate known as TERIC 16A30 (Huntsman).

In preferred embodiments of the invention, the tablets comprise a nonylphenyl ethoxylate known as TERIC N9 or TERIC N5 (Huntsman).

In preferred embodiments of the invention, the tablets comprise the non-ionic emulsifier, Tween-80.

In preferred embodiments of the invention, the tablets comprise the cationic emulsifier, cetrimonium chloride.

In preferred embodiments of the present invention, the tablets may comprise two or more different emulsifiers. The two or more different emulsifiers may be different non-ionic emulsifiers, or different anionic emulsifiers, or different cationic emulsifiers, or different zwitterionic emulsifiers or a combination of non-ionic, anionic, cationic and/or zwitterionic emulsifiers.

In preferred embodiments of the invention, the tablets comprise two different types of emulsifiers. In more preferred embodiments of the inventions, the two types emulsifiers are non-ionic emulsifiers and cationic emulsifiers.

In particularly preferred embodiments of the invention, the tablets comprise at least one cationic emulsifier and at least two different non-ionic emulsifiers. In further preferred embodiments of the invention, the tablets comprise one cationic emulsifier and at least three different non-ionic emulsifiers. The tablets may comprise at least four different non-ionic emulsifiers.

In preferred embodiments, the tablets comprise at least three emulsifiers selected from the group consisting of a cetearyl alcohol, a ceteareth, a Tween emulsifier, a nonylphenyl ethoxylate, an alcohol alkoxylate, an alcohol ethoxylate and a quaternary ammonium compound.

In preferred embodiments, the tablets comprise at least four emulsifiers selected from the group consisting of a cetearyl alcohol, a ceteareth, a Tween emulsifier, a nonylphenyl ethoxylate, an alcohol ethoxylate, an alcohol alkoxylate, and a quaternary ammonium compound.

In preferred embodiments, the tablets comprise at least three emulsifiers selected from the group consisting of cetearyl alcohol, ceteareth-20, Tween-80, TERIC® N5, TERIC® N9, TERIC® BL8, TERIC® 16A30 and Cetrimonium chloride.

In embodiments of the invention, the total concentration of emulsifier in the tablets is about 10%-40% or 10%-20% (w/w).

In preferred embodiments, the tablets comprise Emulagade® 1000NI concentration of about 1%-10% (w/w). In preferred embodiments of the invention, the tablets may comprise Emulagade® 1000NI at a concentration of about 1%-5% (w/w).

In embodiments of the invention, the total concentration of cationic emulsifier in the tablets is about 1%-10% (w/w). In preferred embodiments, the total concentration of cationic emulsifier in the tablets is about 4%-6%, 5%-7%, 6%-8%, or 7%-8% (w/w).

In preferred embodiments, the cationic emulsifier in the tablets is cetrimonium chloride and is present at a concentration of about 4%-5, 5%-6%, 6%-7%, or 7%-8% (w/w).

In embodiments of the invention, the total concentration of non-ionic emulsifier in the tablets is about 5%-30% (w/w). In preferred embodiments, the total concentration of non-ionic emulsifier in the tablets is about 10%-20% or 10%-15% (w/w).

In preferred embodiments, the tablets comprise cetearyl alcohol at a concentration of about 1%-5% (w/w). In preferred embodiments of the invention, the tablets may comprise cetearyl alcohol at a concentration of about 1%-3% (w/w).

In preferred embodiments, the tablets comprise ceteareth at a concentration of about 1%-5% (w/w). In preferred embodiments of the invention, the tablets may comprise ceteareth at a concentration of about 1%-3% (w/w).

In preferred embodiments, the tablets comprise a Tween emulsifier at a concentration of about 1%-10% (w/w). In preferred embodiments of the invention, the tablets may comprise a Tween emulsifier at a concentration of about 4%-7% (w/w).

In preferred embodiments, the tablets comprise alcohol alkoxylate at a concentration of about 1%-10% (w/w). In preferred embodiments of the invention, the tablets may comprise alcohol alkoxylate at a concentration of about 4%-7% (w/w).

In preferred embodiments, the tablets comprise alcohol ethoxylate at a concentration of about 1%-15% (w/w). In preferred embodiments of the invention, the tablets may comprise alcohol ethoxylate at a concentration of about 5%-10%, 4%-8% or 5%-7% (w/w).

In preferred embodiments, the tablets comprise nonylphenyl ethoxylate at a concentration of about 0.2%-10% (w/w). In preferred embodiments of the invention, the tablets comprise nonylphenyl ethoxylate at a concentration of about 0.5%-3%, 3%-7% (w/w).

In very preferred embodiments of the invention, the tablets may comprise at least three emulsifiers selected from the group consisting of Emulagade® 1000N1 at a concentration of about 2%-4% (w/w), cetrimonium chloride at a concentration of about 4%-6% (w/w), Tween-80 at a concentration of about 4%-6% (w/w), TERIC® N5 at a concentration of about 3%-6% (w/w), TERIC® N9 at a concentration of about 0.5%-2% (w/w), and TERIC® BL8 at a concentration of about 4%-6% (w/w).

In very preferred embodiments of the invention, the tablets may comprise at least three emulsifiers selected from the group consisting of Emulagade® 1000NI at a concentration of about 3%-5% (w/w), cetrimonium chloride at a concentration of about 6%-8% (w/w), TERIC® N9 at a concentration of about 0.5%-2% (w/w), and TERIC® 16A30® at a concentration of about 4%-6% (w/w).

The thickening agent used in the tablets of the present invention may be any compound or composition suitable for sufficiently solidifying the mixture such that it may be formed into a solid tablet. The thickening agent may be a non-aqueous phase thickener and may be a carbohydrate-rich, mineral-rich or lipid-rich agent.

The mineral-rich thickening agent may be selected from the group selected from inorganic and/or hydrophilic clays or silicas. Non-limiting examples include bentonite clays, attapulgite clays, organoclays and hectorite clays.

The thickening agent may be a carbohydrate-rich agent such as cellulose, xantham or gelatine. In embodiments of the invention, the thickening agent is arrowroot powder.

More preferably, the thickening agent is a lipid-rich agent. Non-limiting examples of lipid-rich thickening agents include beeswax and hydrogenated castor oil, also known as carbowax and/or PEG-40.

It would be understood that hydrogenated castor oil, being a water soluble wax, allows for a solid bind of the tablet whilst dissolving quickly in water.

In preferred embodiments of the invention, the tablets may comprise the thickening agent at a concentration of about 1%-15% (w/w). More preferably, the tablets comprise hydrogenated castor oil at a concentration of about 5%-15%, 1%-1-%, 1%-5% or 1%-3% (w/w).

The oil in the tablets of the present invention may be any oil suitable for use with hair, and may be any mixture of any number of different oils. In preferred embodiments, the tablets may comprise at least 2%, at least 5%, at least 10%, at least 15%, at least 20%, or at least 30% (w/w) oil.

The oil in the tablets of the present invention may be any oil derived from any oil-producing plant, and may be any mixture of any number of different plant oils. In preferred embodiments, the tablets may comprise at least 2%, at least 5%, at least 10%, at least 15%, at least 20%, or at least 30% (w/w) plant oil.

In preferred embodiments, the tablets may comprise about 15%-20%, 15%-25%, 20%-25% or 25%-25% (w/w) plant oil.

The plant oils used may be oils that have natural moisturizing properties. In preferred embodiments of the invention, the total plant oil comprises at least one other plant oil selected from the group consisting of coconut oil, shea oil/butter, olive oil, almond oil, peppermint oil, apricot kernel oil, tulsi oil, lemon grass oil, lavender oil, sunflower seed oil, wheat germ oil, argan oil, *camellia* oil, castor seed oil, macadamia oil, meadowfoam seed oil, hemp seed oil, jojoba oil, grape seed oil, marula oil, rice bran oil, avocado oil, raspberry seed oil, citrus oil and carrot seed oil.

In preferred embodiments of the invention, the tablets comprise coconut oil. In particularly preferred embodiments of the invention, the tablets may comprise up to 20% (w/w) coconut oil. In preferred embodiments, the tablets may comprise at least 2%, at least 5%, at least 7%, or at least 10% (w/w) coconut oil. In other preferred embodiments, the tablets may comprise about 1%-5% or 3%-5% (w/w) coconut oil.

In preferred embodiments of the invention, in addition to the coconut oil, the total plant oil comprises at least one oil selected from the group consisting of macadamia oil, shea oil/butter, olive oil, peppermint oil, wheat germ oil, marula oil, argan oil, *camellia* oil, castor seed oil, jojoba oil, raspberry seed oil, and carrot seed oil.

In a preferred embodiment of the invention, the present invention is a water disintegratable tablet used for cosmetic purposes, which may include hair treatments, comprising one or more emulsifiers at a concentration of about 10%-40% (w/w), a lipid-rich thickening agent at a concentration of about 1%-15% (w/w), one or more plant oils at a concentration of about 15%-25% (w/w), and a water soluble, organic rheology modifier at a concentration of about 30%-45% (w/w).

In a preferred embodiment of the invention, the present invention is a water disintegratable tablet used for hair treatments, comprising one or more cationic and/or nonionic emulsifiers at a concentration of about 10%-20% (w/w), a lipid-rich thickening agent at a concentration of about 1%-5% (w/w), one or more plant oils at a concentration of about 15%-25% (w/w), and a water soluble, organic rheology modifier at a concentration of about 40%-45% (w/w).

In a preferred embodiment of the invention, the present invention is a water disintegratable tablet used for hair treatments, comprising one or more cationic and/or non-ionic emulsifiers at a concentration of about 10%-20% (w/w), hydrogenated castor oil at a concentration of about 1%-5% (w/w), one or more plant oils at a concentration of about 15%-25% (w/w), and a glycerol ester at a concentration of about 20%-45% (w/w).

It would be understood by the person skilled in the art that the tablets of the invention can also include preservatives, antiseptics, emollients, protein extracts, ultraviolet radiation (UVR) filtering agents, fragrance, active agents, excipients, diluents and colouring agents.

The emollient used in the tablet of the present invention may be any compound or composition that may assist in forming an at least partially waterproof layer on a hair shaft that may assist in the prevention of evaporation of water from the hair shaft. The emollient may be a lipid-based or silicone-based emollient.

In preferred embodiments of the invention, the tablets may comprise an emollient at a concentration of about 5%-20% (w/w). More preferably, the tablets may comprise an emollient at a concentration of about 5%-15% (w/w). In other preferred embodiments, the tablets may comprise an emollient at a concentration of about 6%-12% or 5%-10% (w/w).

In very preferred embodiments of the invention, the tablets comprise cetiol-C5 at a concentration of about 5%-15%, 5%-1-% or 7%-10% (w/w).

The protein extract used in the tablets of the present invention may be any extract comprising proteins, peptides and/or amino acids that are suitable for use on the hair and may assist worth the strengthening of the hair shaft.

The protein extract may be any hydrolysed protein extracts, silk-based protein extracts, plant-based protein extracts, including but not limited to such as hydrolysed silk, keratin, wheat protein, collagen and soy protein.

In preferred embodiments of the invention, the tablets may comprise the protein extract at a concentration of about 0.5%-5% (w/w).

In very preferred embodiments of the invention, the tablets comprise hydrolysed soy protein at a concentration of about 0.5% to 3% (w/w).

In very preferred embodiments of the invention, the tablets comprise hydrolysed keratin at a concentration of about 0.5% to 3% (w/w).

The preservative used in the tables of the present invention may be any substance that assists in the prevention of microbial growth and degradation of the tablet.

The preservative may be an anti-microbial or an anti-oxidant. In preferred embodiments of the invention, the tablets may comprise a preservative at a concentration of 0.5%-5% (w/w). More preferably, the tablets may comprise a preservative at a concentration of 1%-3% (w/w).

In very preferred embodiments of the invention, the tablets comprise phenoxyethanol and/or sodium benzoate at a concentration of 0.5%-3% (w/w).

The UVR filtering agent used in the tablets of the present invention may be any compound that has the capacity to absorb, block or reflect UVR, wherein the UVR occurs at a wavelength within the range of about 280 nm to about 400 nm. It would be understood by the person skilled in the art that this wavelength range encompasses both the UVA and UVB wavelength range.

The UVR filtering agent may predominantly absorb, block or reflect UVA or UVB, or it may be a broad spectrum UVR filtering agent that absorbs, blocks or reflects UVR occurring at wavelengths that fall within both the UVA and UVB ranges.

The UVR filtering agent may be a chemical sunscreening agent or a physical sunscreening agent. The choice of UVR filtering agent or agents used in the tablets would be influenced by factors such as safety and regulatory considerations, whether the agents were liquid or solid, and the capability of the UVR filtering agent(s) to be combined with the other components to form a water soluble cosmetic tablet.

In preferred embodiments, the UVR filtering agent may be a commercially available UVR filtering agent selected from the group consisting of (using the Australian Approved Names (AAN)) Bemotrizinol (Bis-ethylhexyloxyphenol methoxyphenol triazine, Bemotrizinolum, Escalol S, Tinosorb S, 10%), Benzylidene camphor sulfonic acid (alpha-(2-Oxoborn-3-ylidene)toluene-4-sulphonic acid, Meroxyl SL, 6%), Butyl methoxy dibenzoylmethane (BMDM, 4-tert-butyl-4'-methoxy dibenzoylmethane, 1-(4 tert butylphenyl)-3(4-methoxyphenyl)-propane-1,3-dione, Avobenzone, 5%), Camphor benzalkonium methosulfate (N,N,N-Trimethyl-4-(oxoborn-3-ylidenemethyl)anilinium methyl sulphate, Meroxyl SO, 6%), Cinoxate (2-Ethoxyethyl para-methoxycinnamate, 6%), Diethylamino hydroxybenzoyl hexyl benzoate (Benzoic acid, 2-[4-(diethylamino)-2-hydroxybenzoyl]-hexyl ester, Uvinul A Plus, 10%), Dioxybenzone (Benzophenone 8, 3%), Disodium phenyl dibenzimidazole tetrasulfonate (1H-Benzimidazole-4,6-disulfonic acid,2,2'-(1,4-phenylene)bis-,disodium salt, Bisimidazylate, Neo Heliopan AP, 10%), Drometrizole trisiloxane (2-(2H-Benzotriazol-2-yl)-4-methyl-6[2-methyl-3-[1,3,3,3-tetramethyl-1-[(trimethylsilyl)oxy]-disiloxanyl]-propylphenol, Silatrizole, Mexoryl XL, 15%), Ecamsule (Terephthalylidene dicamphor sulfonic acid, Mexoryl SX, 10%), Homosalate (Homomenthyl salicylate, 3,3,5-Trimethylcyclohexyl 2-hydroxybenzoate, 15%), Isoamyl methoxy-cinnamate (Isoamyl p-methoxycinnamate, Isoamyl-4-methoxycinnamate, Isopentenyl-4-methoxycinnamate, Amiloxate, 10%), 4-Methylbenzylidene camphor (3-(4-Methylbenzylidene)-dl-camphor, Enzacamene, 4%), Menthyl anthranilate (Menthyl 2-aminobenzoate, 5-Methyl-2-(1-methylethyl) cyclohexanol-2-aminobenzoate, Meradimate, 5%), Methylene bis-benzo-triazolyl-tetramethyl-butylphenol (2,2'-Methylene-bis-6-(2H-benzotriazol-2yl)-4-(tetramethyl-butyl)-1,1,3,3-phenol, Bisoctrizole, Tinosorb M, 10%), Octocrylene (Octocrilene, 2-cyano-3,3-diphenyl acrylic acid, 2-ethyl hexyl ester, 2-Ethylhexyl-2-cyano-3,3 diphenylacrylate, Uvinul N, 10%), Octyl methoxy-cinnamate (Ethylhexyl methoxycinnamate, Octinoxate, Uvinul MC, 10%), Octyl salicylate (Ethylhexyl salicylate, 2-Ethylhexyl salicylate, Octisalate, 5%), Octyl triazone (Ethylhexyl triazone, 2,4,6-Trianalino-(p-Carbo-2'-ethylhexyl-1'oxy)-1,3,5-triazine, Uvinul T, 5%), Padimate O (Ethylhexyl dimethyl PABA, 2-Ethylhexyl 4-dimethylaminobenzoate, Octyl dimethyl PABA, 8%), PEG-25 PABA (Ethoxylated ethyl 4-aminobenzoate, PEG25 PABA, Uvinul P, 10%), Phenylbenzimidazole sulfonic acid (-Phenylbenzimidazole-5-sulfonic acid, 2-Phenyl-5-sulfobenzimidazole, Ensulizole, 4%), Polysilicone-15 (Dimethicodiethylbenzalmalonate, Diethylbezylidene malonate dimethicone, Diethylmalonylbenzylidene oxypropene dimethicone, Parsol SLX, 10%), Sulisobenzone (Benzophenone 4, 5-Benzoyl-4-hydroxy-2-methoxybenzene sulphonic acid, Uvinul MS, 10%), Sulisobenzone sodium (Benzophenone 5, 5-Benzoyl-4-hydroxy-2-methoxybenzene sulphonic acid, sodium salt, 10%), Titanium dioxide (E171, 25%), Triethanolamine salicylate (TEA-salicylate, Trolamine salicylate, 12%), Zinc oxide (Pigment white 4, no limit) (wherein the brackets included synonyms, abbreviations, trade names, and maximum concentrations allowed in Australia).

The preceding list is a compilation of UVR filtering agents approved for use in Australia and this list may change over time to exclude some compounds, while new compounds may be included. It would be understood that any compounds added to the list would also be suitable UVR filtering agents for use in the present invention.

In preferred embodiments, the UVR filtering agent is ethylhexyl methoxycinnamate.

In preferred embodiments of the invention, the tablets may comprise one or more UVR filtering agents in a concentration of less than 10% (w/w). More preferably, the tablets may comprise one or more UVR filtering agents in a concentration of less than 5% (w/w). In other preferred embodiments, the tablets may comprise one or more UVR filtering agents in a concentration of less than 3% (w/w) or about 0.5%-2% (w/w).

In various embodiments of the invention, the tablets are formulated to provide particular treatments to the hair, such as, for example, strengthening treatment, colour care treatment or hydration treatment. It would be understood that in order to provide different treatments to hair, the specific formulation of each tablet may be modified.

Accordingly, in a particularly preferred embodiment of the present invention, there is provided a water distintegratable strengthening treatment tablet for strengthening the hair shaft comprising an emulsifier, a thickening agent, an oil and a rheology modifier, wherein the oil is a protein-rich oil.

In preferred embodiments, the strengthening treatment tablet further comprises a protein extract.

In further preferred embodiments, the protein-rich oil is argan oil, marula oil or camelia oil.

In preferred embodiments of the invention, the strengthening treatment tablet comprises a non-ionic emulsifier, a cationic emulsifier, a water-soluble organic polymeric rheology modifier, a lipid-rich thickening agent, a protein extract, a protein-rich oil and at least one other plant oil.

In preferred embodiments of the invention, the strengthening treatment tablet comprises a combination of at least three emulsifiers. In more preferred embodiments, the hair strengthening tablet comprises a total concentration of emulsifier of at least 15%, at least 20% or at least 25% (w/w).

In preferred embodiments of the invention, the strengthening treatment tablet comprises emulsifier at a concentration of about 20%-25% (w/w), a water-soluble organic polymeric rheology modifier at a concentration of about 25%-35% (w/w), a lipid-rich thickening agent at a concentration of about 4%-7% (w/w), argan oil at a concentration of about 5%-15% (w/w) and at least one other plant oil at a concentration of about 10%-15% (w/w).

In other preferred embodiments of the invention, the strengthening treatment tablet comprises emulsifier at a concentration of about 15%-20% (w/w), a water-soluble organic polymeric rheology modifier at a concentration of about 40%-45% (w/w), a lipid-rich thickening agent at a concentration of about 1%-3% (w/w), a protein extract at a concentration of about 0.5%-2% (w/w), a protein-rich oil at a concentration of about 1%-5% (w/w) and at least one other plant oil at a concentration of about 5%-15% (w/w).

In other preferred embodiments of the invention, the strengthening treatment tablet comprises emulsifier at a concentration of about 15%-20% (w/w), a water-soluble organic polymeric rheology modifier at a concentration of about 40%-45% (w/w), a lipid-rich thickening agent at a concentration of about 1%-3% (w/w), a protein extract at a concentration of about 0.5%-2% (w/w), a protein-rich oil at a concentration of about 1%-5% (w/w), at least one other plant oil at a concentration of about 5%-15% (w/w) and an emollient at a concentration of about 5%-10% (w/w).

In preferred embodiments of the invention, the strengthening treatment tablet comprises cetearyl alcohol, ceteareth, PEG-4000, cetiol-C5, coconut oil, Tween-80, shea butter, argan oil, TERIC® N9, TERIC® N5, TERIC® BL8, olive oil, cetrimonium chloride, hydrogenated castor oil and phenoxyethanol.

In further preferred embodiments of the invention, the strengthening treatment tablet comprises cetearyl alcohol, ceteareth, PEG-4000, cetiol-C5, coconut oil, shea butter, argan oil, marula oil, camelia oil, soy bean extract, TERIC® N9, TERIC® 16A30, olive oil, cetrimonium chloride, hydrogenated castor oil and phenoxyethanol.

In a particularly preferred embodiment of the present invention, there is provided a water disintegratable colour care tablet for maintaining the colour of colour-treated hair comprising an emulsifier, a thickening agent, a rheology modifier and a UVR filtering agent.

In further preferred embodiments, the UVR filtering agent is ethylhexyl methoxycinnamate.

In preferred embodiments of the invention, the colour care tablet comprises a non-ionic emulsifier, a cationic emulsifier, a water-soluble organic polymeric rheology modifier, a lipid-rich thickening agent, at least one plant oil and a UVR filtering agent.

In preferred embodiments of the invention, the colour care tablet comprises a combination of at least three emulsifiers. In more preferred embodiments, the colour care tablet comprises a total concentration of emulsifier of at least 10%, at least 15% or at least 20% (w/w).

In preferred embodiments of the invention, the colour care tablet comprises emulsifier at a concentration of about 15%-20% (w/w), a water-soluble organic polymeric rheology modifier at a concentration of about 30%-40% (w/w), a lipid-rich thickening agent at a concentration of about 8%-13% (w/w), a UVR filtering agent at a concentration of about 2%-10% (w/w) and plant oil at a concentration of about 10%-20% (w/w).

In other preferred embodiments of the invention, the colour care tablet comprises emulsifier at a concentration of about 15%-20% (w/w), a water-soluble organic polymeric rheology modifier at a concentration of about 40%-45% (w/w), a lipid-rich thickening agent at a concentration of about 1%-3% (w/w), a UVR filtering agent at a concentration of about 0.5%-5% (w/w) and plant oil at a concentration of about 10%-20% (w/w).

In other preferred embodiments of the invention, the colour care tablet comprises one or cationic and/or non-ionic emulsifiers at a total concentration of about 15%-20% (w/w), a water-soluble organic rheology modifier at a concentration of about 40%-45% (w/w), a lipid-rich thickening agent at a concentration of about 1%-3% (w/w), a UVR filtering agent at a concentration of about 0.5%-5% (w/w), plant oil at a concentration of about 10%-20% (w/w) and cetiol C5 at a concentration of about 5%-10% (w/w).

In preferred embodiments of the invention, the colour care tablet comprises cetearyl alcohol, ceteareth, PEG-4000, cetiol-C5, coconut oil, macadamia oil, carrot seed oil, shea butter, wheat germ oil, TERIC® N9, TERIC® N5, cetrimonium chloride, hydrogenated castor oil, phenoxyethanol and ethylhexyl methoxycinnamate.

In preferred embodiments of the invention, the colour care tablet comprises cetearyl alcohol, ceteareth, PEG-4000, cetiol-C5, coconut oil, almond oil, raspberry seed oil, argan oil, macadamia oil, carrot seed oil, shea butter, wheat germ oil, TERIC® N9, TERIC® 16A30, cetrimonium chloride, hydrogenated castor oil, phenoxyethanol and ethylhexyl methoxycinnamate.

In a particularly preferred embodiment of the present invention, there is provided a water disintegratable hydration tablet for maintaining the moisture level of hair comprising an emulsifier, a thickening agent, and a rheology modifier.

In preferred embodiments of the invention, the hydration tablet comprises a non-ionic emulsifier, a cationic emulsifier, a water-soluble organic polymeric rheology modifier, a lipid-rich thickening agent and at least one plant oil.

In preferred embodiments of the invention, the hydration tablet comprises a combination of at least three emulsifiers. In more preferred embodiments, the hydration tablets comprise a total concentration of emulsifier of at least 10% or at least 15% (w/w).

In preferred embodiments of the invention, the hydration tablet comprises emulsifier at a concentration of about 15%-20% (w/w), a water-soluble organic polymeric rheology modifier at a concentration of about 35%-45% (w/w), a lipid-rich thickening agent at a concentration of about 10%-15% (w/w) and plant oil at a concentration of about 15%-25% (w/w).

In further preferred embodiments of the invention, the hydration tablet comprises emulsifier at a concentration of about 15%-20% (w/w), a water-soluble organic polymeric rheology modifier at a concentration of about 40%-45% (w/w), a lipid-rich thickening agent at a concentration of about 1%-3% (w/w) and plant oil at a concentration of about 10%-20% (w/w).

In further preferred embodiments of the invention, the hydration tablet comprises one or more cationic and/or non-ioninc emulsifiers at a total concentration of about 15%-20% (w/w), a water-soluble organic rheology modifier at a concentration of about 40%-45% (w/w), hydrogenated castor oil at a concentration of about 1%-3% (w/w), plant oil at a concentration of about 10%-20% (w/w) and an emollient at a concentration of about 5%-10% (w/w).

In preferred embodiments of the invention, the hydration tablet comprises cetearyl alcohol, ceteareth, PEG-4000, cetiol-C5, coconut oil, macadamia oil, carrot seed oil, shea butter, olive oil, TERIC® N9, TERIC® N5, cetrimonium chloride, hydrogenated castor oil and phenoxyethanol.

In preferred embodiments of the invention, the hydration tablet comprises cetearyl alcohol, ceteareth, PEG-4000, cetiol-C5, coconut oil, macadamia oil, carrot seed oil, shea butter, olive oil, argan oil, almond oil, castor oil, jojoba oil, TERIC® N9, TERIC® 16A30, cetrimonium chloride, hydrogenated castor oil and phenoxyethanol.

In a third aspect of the present invention, there is also provided a water soluble cleansing tablet for cleaning the hair comprising a foaming agent, a non-ionic surfactant and a disintegrant.

The cleansing tablet preferably a pressed dry tablet that dissolves in water. Preferably, the cleansing tablet is for use prior to treating the hair with one or more of the treatment tablets.

In embodiments of the invention, the cleansing tablets also comprise mixtures of buffering salts such as phosphates, citrates, calcium slats, carbonates and silicates at percentages ranging from 5%-30% (w/w).

In embodiments of the invention, the cleansing tablets also comprise an essential oil. Preferably, the essential oil is peppermint oil at a percentage ranging from 5%-30%, 5%-10%, 10%-30% or 10%-20% (w/w).

The foaming agent may be any surfactant capable of creating a lather. Preferably, the foaming agent is an anionic surfactant.

In embodiments of the invention, the anionic surfactant in the cleansing tablet is selected from the group consisting of sodium C14-C16 olefin sulfonate, sodium laureth sulphate, sodium cocoyl isethionate, sodium lauryl sulfoacetate, disodium laureth sulfosuccinate and sodium methyl cocoyl taurate.

The foaming agent is preferably a solid. In embodiments of the cleansing tablet, the tablet comprises about 10%-70% (w/w) foaming agent. In preferred embodiments, the tablets comprise about 20%-30%, 25%-50%, 20%-40%, 30%-50%, 40%-60% or 50%-70% (w/w) foaming agent.

In preferred embodiments, the anionic surfactant is sodium cocoyl isethionate or sodium lauryl sulfoacetate or a combination of sodium cocoyl isethionate and sodium lauryl sulfoacetate.

In embodiments, the cleansing tablets comprise about 20%-30%, 30%-40%, 40%-50%, 50%-60% or 60%-70% (w/w) sodium cocoyl isethionate or sodium lauryl sulfoacetate or a combination of sodium cocoyl isethionate and sodium lauryl sulfoacetate.

Preferably, the cleansing tablets comprise about 20%, 30%, 40%, 50%, 60% or 70% (w/w) sodium cocoyl isethionate or sodium lauryl sulfoacetate or a combination of sodium cocoyl isethionate and sodium lauryl sulfoacetate.

The disintegrant may be any compound that assists in the disintegration of the tablet in water. The disintegrant may assist in the disintegration of the tablet in water by expanding when exposed to water such that the tablet starts to break apart, facilitating dissolution.

In embodiments of the invention, the disintegrant is a cross-linked polymer or a modified starch or cellulose product.

Preferably, the disintegrant is a crosslinked polymer. In preferred embodiments of the invention, the crosslinked polymer is polyvinylpyrrolidone.

In other preferred embodiments, the disintegrant is microcrystalline cellulose.

In embodiments of the cleansing tablet, the tablet comprises 0.1%-10% (w/w) disintegrant. In preferred embodiments, the tablets comprise 0.1%-5% (w/w) disintegrant. Preferably, the cleansing tablets comprise 1%-5% (w/w) polyvinylpyrrolidone. In other preferred embodiments, the cleansing tablets comprise 0.1%-3% microcrystalline cellulose.

The non-ionic surfactant may be any non-charged surfactant compound that assists in the wetting of the tablet in water by lowering the surface tension between the water and the tablet. The non-ionic surfactant may also contribute to the foaming properties of the tablet.

In embodiments of the invention, the non-ionic surfactant is an alcohol polyethylene glycol ether.

In other embodiments of the invention, the non-ionic surfactant is a amphipathic glycoside belonging to the saponin family.

In preferred embodiments of the invention, the alcohol polyethylene glycol ether is alkyl polyethylene glycol ether.

In embodiments of the cleansing tablet, the tablet comprises 10%-40% (w/w) non-ionic surfactant. In preferred embodiments, the tablets comprise 10%-20%, 5%-15% or 20%-30% (w/w) non-ionic surfactant.

Preferably, the cleansing tablets may comprise 20%-30% (w/w) alkyl polyethylene glycol ether.

Preferably, the cleansing tablets may comprise 10%-15% (w/w) or one or more saponin.

In a preferred embodiment of the invention, the cleansing tablets comprise an anionic surfactant, a cross-linked polymer and alcohol polyethylene glycol. In particularly preferred embodiments, the cleansing tablets comprise 20%-30% (w/w) sodium cocoyl isethionate, 1%-5% (w/w) polyvinylpyrrolidone, 20%-30% (w/w) alkyl polyethylene glycol ether and buffered salts.

In a preferred embodiment of the invention, the cleansing tablets comprise an anionic surfactant, microcrystalline cellulose and one or more saponins. In particularly preferred embodiments, the cleansing tablets comprise 50%-60% (w/w) sodium cocoyl isethionate, 0.1%-3% (w/w) microcrystalline cellulose, 10%-20% (w/w) saponin and buffered salts.

In a preferred embodiment of the invention, the cleansing tablets comprise an anionic surfactant, microcrystalline cellulose and a saponin. In particularly preferred embodiments, the cleansing tablets comprise 50%-60% (w/w) sodium cocoyl isethionate, 1%-10% (w/w) sodium lauryl sulpacetate, 0.1%-3% (w/w) of a modified cellulose product, 10%-15% (w/w) saponin and buffered salts.

It would be understood by the person skilled in the art that the cleansing tablets of the invention can also include preservatives, antiseptics, emollients, fragrance, active agents, excipients, diluents and colouring agents.

The tablets of the present invention may be manufactured in any shape or size suitable for use in the shower head apparatus of the present invention. Preferably, the tablets are about 3-7 grams. More preferably, the tablets are about 5 grams.

In a fourth aspect of the present invention, there is also provided a treatment spray for use after cleaning and/or treating the hair with one or more of the tablets of the present invention comprising a non-ionic emulsifier, a cationic emulsifier and a cationic silicone emulsion.

In embodiments of the present invention, the treatment spray further comprises a preservative. The preservative may be any preservative as previously described. Preferably, the preservative is phenoxyethanol.

In embodiments of the present invention, the treatment spray comprises 0.1%-5% (w/w) preservative. Preferably, the treatment spray comprises 0.1%-0.5% (w/w) phenoxyethanol.

The non-ionic emulsifier may be any non-ionic emulsifier as previously described. Preferably, the non-ionic emulsifier is a Tween emulsifier.

In preferred embodiments of the invention, the treatment spray comprises the non-ionic emulsifier, Tween-20.

In embodiments of the invention, the concentration of non-ionic emulsifier in the treatment spray is about 0.1%-10% (w/w). In preferred embodiments, the concentration of non-ionic emulsifier in the treatment spray is about 0.5%-5% (w/w).

In preferred embodiments, the treatment spray comprises a Tween emulsifier at a concentration of about 0.5%-5% (w/w). In preferred embodiments of the invention, the treatment spray comprises Tween-20 at a concentration of about 1%-3% (w/w).

The cationic emulsifier may be any cationic emulsifier as previously defined. In embodiments of the invention, the cationic emulsifier is a quaternary amine emulsifier selected from the group consisting of benzalkonium chloride, benzethonium chloride, stearalkonium chloride and cetrimonium chloride.

In preferred embodiments of the invention, the treatment spray comprises cetrimonium chloride.

In embodiments of the invention, the concentration of cationic emulsifier in the treatment spray is about 5%-20% (w/w). In preferred embodiments, the concentration of cationic emulsifier in the treatment spray is about 10%-15% (w/w).

In preferred embodiments, the cationic emulsifier in the treatment spray is cetrimonium chloride and is present at a concentration of about 10%-15% (w/w).

The cationic silicone emulsion may be any stabilised positively charged emulsion comprising silicone, a cationic amine emulsifier and a rheology modifier. It would be understood that the positively charge emulsion would have an affinity for negatively charged hair.

In preferred embodiments, the treatment spray comprises about 5%-15% (w/w) cationic silicone emulsion.

The silicone is an amine-functionalised silicone polymer and may be any polymer selected from the group consisting of aminopropyl dimethicone, amodimethicone, bis-aminopropyl dimethicone, dimethicone and trimethyl silylamodimethicone. Preferably, the amine-functionalised silicone polymer in the cationic silicone emulsion is amodimethicone.

In preferred embodiments of the invention, the cationic silicone emulsion may comprise an amine-functionalised silicone polymer at a concentration of about 5%-50% (w/w). More preferably, the cationic silicone emulsion comprises an amine-functionalised silicone polymer at a concentration of about 20%-50% (w/w). In further preferred embodiments, the cationic silicone emulsion comprises an amine-functionalised silicone polymer at a concentration of about 30%-40% (w/w).

In particularly preferred embodiments, the cationic silicone emulsion comprises amodimethicone at a concentration of about 30%-40% (w/w).

In other preferred embodiments of the present invention, the cationic silicone emulsion comprises amodimethicone at a concentration of about 30%, 35% or 40% (w/w).

The rheology modifier may be any rheology modifier as previously defined and it would be understood the rheology modifier helps stabilise the cationic silicone emulsion. Preferably, the rheology modifier is an ether of a polyethylene glycol, such as, for example, a tridecyl ether of polyethylene glycol.

The cationic amine emulsifier may be any cationic amine emulsifier as previously defined. Preferably, the cationic amine emulsifier is cetrimonium chloride.

In a preferred embodiment of the invention, the treatment spray comprises a Tween emulsifier, a quaternary amine emulsifier and a cationic silicone emulsion. In particularly preferred embodiments, the treatment spray comprises 1%-3% (w/w) Tween-20, 10%-15% (w/w) cationic silicone emulsion, 10%-15% (w/w) cetrimonium chloride and a preservative.

In a fifth aspect of the present invention, there is also provided a cream spray for use after cleaning and/or treating the hair with one or more of the tablets of the present invention comprising an anionic emulsifier, a cationic emulsifier, a thickening agent and a plant oil.

The cationic emulsifier may be any cationic emulsifier as previously defined. Preferably, the cationic emulsifier is cetrimonium chloride.

In embodiments of the invention, the total concentration of cationic emulsifier in the cream spray is about 1%-10% (w/w). In preferred embodiments, the total concentration of cationic emulsifier in the cream spray is about 1%-7%, 2%-6%, 3%-5%, or about 4% (w/w).

In preferred embodiments, the cationic emulsifier in the tablets is cetrimonium chloride and is present at a concentration of about 1%-2%, 2%-3%, 3%-5%, 4%-6% or 8%-10% (w/w).

The anionic emulsifier may be any anionic emulsifier as previously defined.

Preferably, the anionic emulsifier is a glycerol ester or a derivative thereof, such as, for example, glyceryl stearate citrate. In other embodiments, the anionic emulsifier is sodium cocoyl isethionate. In further embodiments, the anionic emulsifier is a combination of a glycerol ester or a derivative thereof, and sodium cocoyl isethionate.

In particularly preferred embodiments, the cream spray of the present invention comprises a glycerol ester and/or centrimonium chloride at a concentration of about 1%-10%, 5%-20%, 1%-5, 3%-8% or 8%-10% (w/w).

In particularly preferred embodiments, the cream spray of the present invention comprises glyceryl stearate or a derivative thereof at a concentration of about 3%, 4%, 5%, 6%, 7% or 10% (w/w).

In particularly preferred embodiments, the cream spray of the present invention comprises centrimonium chloride at a concentration of about 1%, 2%, 2%, 4%, 5%, 6%, 7%, 8% or 9% or 10% (w/w).

The thickening agent may be any thickening agent as previously defined. Preferably, the thickening agent is a lipid-rich agent, such as, for example, hydrogenated castor oil.

In preferred embodiments of the invention, the tablets may comprise the thickening agent at a concentration of about 0.5%-15% (w/w). More preferably, the tablets comprise hydrogenated castor oil at a concentration of about 5%-15%, 1%-1-%, 1%-5% or 2%-4% (w/w).

The plant oil may be any plant oil as previously defined. In preferred embodiments of the invention, plant oil comprises at least one oil selected from the group consisting of macadamia oil, olive oil, jojoba oil, raspberry seed oil, and almond oil.

In preferred embodiments, the cream spray may comprise at least 2%, at least 5%, at least 10%, at least 15%, at least 20%, or at least 30% (w/w) plant oil.

In other preferred embodiments, the cream spray may comprise about 5%-20% or 5%-15% (w/w) plant oil.

In embodiments, the cream spray further comprises and an emollient. The emollient may be any emollient as previously defined. Preferably, the emollient is Cetiol C5. In preferred embodiments of the invention, the cream spray may comprise an emollient at a concentration of about 5%-20% (w/w). More preferably, the cream spray may comprise an emollient at a concentration of about 5%-15% (w/w). In other preferred embodiments, the cream spray may comprise an emollient at a concentration of about 6%-12% (w/w). In further preferred embodiments of the invention, the cream spray comprises cetiol-C5 at a concentration of about 5%-15%, 5%-10% or 10%-12% (w/w).

In a preferred embodiment of the invention, the cream spray comprises 1%-5% (w/w) centrimonium chloride, 1%-5% (w/w) glyceryl stearate citrate, 1%-3% (w/w) sodium cocoyl isethionate, 1%-5% hydrogenated castor oil and 5%-10% plant oil.

In a preferred embodiment of the invention, the cream spray comprises 1%-10% (w/w) cationic emulsifier, 1%-5% (w/w) glyceryl stearate citrate, 1%-5% (w/w) anionic emulsifier, 1%-10% rheology modifier, 5%-10% plant oil and 5%-10% (w/w) emollient.

In a sixth aspect of the present invention, there is also provided a finishing spray for use after cleaning and/or treating the hair with one or more of the tablets of the present invention comprising a silicone or derivative thereof, a UVR filtering agent, and a plant oil.

The silicone may be any silicone product or derivative thereof suitable for hair treatments. In non-limiting examples, the silicone is an organosilicon compound.

In preferred embodiments, the silicone or derivative thereof is water insoluble, or at least partially water insoluble. Non-limiting example of water insoluble or partially water insoluble silicones include cetearyl methicone, cetyl dimethicone, cyclopentasiloxane, dimethicone, phenyl trimethicone, stearyl dimethicone, trimethyl silylamodimethicone, amodimethicone, cyclohexasiloxane, aminopropyl dimethicone, and bis-aminopropyl dimethicone In preferred embodiments of the invention, the silicone or derivative thereof is cyclopentasiloxane. In preferred embodiments, the finishing spray comprises at least 10%, at least 20%, at least 30%, at least 40%, at least 70%, or at least 80% (w/w) organosilicon. In other preferred embodiments, the finishing spray comprises about 20%-60% or 50%-90% (w/w) of an organosilicon compound that is water insoluble or at least partially water insoluble. In preferred embodiments of the invention, the silicone or derivative thereof is cyclopentasiloxane. In preferred embodiments, the finishing spray comprises at least 10%, at least 20%, at least 30%, at least 40%, at least 70%, or at least 80% (w/w) cyclopetasiloxane.

The plant oil may be any plant oil as previously defined. In preferred embodiments of the invention, the plant oil comprises at least one oil selected from the group consisting of raspberry seed oil, carrot seed oil and wheat germ oil.

In preferred embodiments, the finishing spray comprises at least 1%, at least 2%, at least 3%, at least 4%, at least 7%, or at least 10% (w/w) plant oil. In other preferred embodiments, the finishing spray may comprise about 1%-10% or 1%-5% (w/w) plant oil.

The UVR filter agent may be any filtering agent as previously defined. In preferred embodiments of the invention, the finishing spray may comprise one or more UVR filtering agents in a concentration of less than 10% (w/w). More preferably, the finishing spray may comprise one or more UVR filtering agents in a concentration of less than 5% (w/w). In other preferred embodiments, the finishing may comprise one or more UVR filtering agents in a concentration of less than 3% (w/w) or about 0.5%-2% (w/w).

In embodiments, the finishing spray further comprises and an emollient. The emollient may be any emollient as previously defined. Preferably, the emollient is Cetiol C5. In preferred embodiments of the invention, the finishing spray may comprise an emollient at a concentration of about 5%-20% (w/w). More preferably, the cream finishing may comprise an emollient at a concentration of about 5%-15% (w/w). In further preferred embodiments of the invention, the finishing spray comprises cetiol-C5 at a concentration of about 5%-15%, 5%-10% or 7%-10% (w/w).

In a preferred embodiment of the invention, the finishing spray comprises 1%-5% (w/w) plant oil, 10%-90% (w/w) organosilicon, 1%-3% (w/w) UV filtering agent and 5%-10% (w/w) emollient.

In a preferred embodiment of the invention, the finishing spray comprises 1%-5% (w/w) plant oil, 10%-90% (w/w) organosilicon, 1%-3% (w/w) UV filtering agent and 5%-10% (w/w) emollient.

In a preferred embodiment of the invention, the finishing spray comprises 1%-5% (w/w) plant oil, 50%-90% (w/w) cyclopentasiloxane, 1%-3% (w/w) UV filtering agent and 5%-10% (w/w) cetiol C5.

It would be understood by the person skilled in the art that any of the sprays of the invention can also include additional preservatives, antiseptics, emollients, fragrance, active agents, excipients, diluents and colouring agents.

Definitions

In the context of the present invention, the words "comprise", "comprising" and the like are to be construed in their inclusive, as opposed to their exclusive, sense, that is in the sense of "including, but not limited to".

BRIEF DESCRIPTION OF THE DRAWINGS

A preferred embodiment(s) of the invention will now be described, by way of example only, with reference to the accompanying drawings(s) in which.

PREFERRED EMBODIMENT OF THE INVENTION

The present invention will now be described with reference to the following examples which should be considered in all respects as illustrative and non-restrictive.

Referring to the drawings there is shown a first embodiment hand held shower head 1 according to the invention. The shower head includes a hollow body portion 2 with a water inlet 3 and water outlet in the form of perforations 4 in a perforated plate 5.

Disposed adjacent the plate 5, there is provided a fixed mesh formation shown generally at 6. The mesh formation 6 is spaced slightly from the perforated plate and preferably includes a bowl like cradle portion 8, which is ideally centrally located. The mesh formation in the illustrated embodiment extends fully across the perforated plate and cradle portion 8 has a generally flat base region 9 and slightly sloping sides 10. This cradle shape acts to generally locate an appropriately sized and shaped treatment tablet 11 when it is first inserted within the shower head prior to use and as it moves toward the perforated plate, and the sloping sides act to help deflect the slowly disintegrating tablet that is forced toward the mesh by the water flow, back into the turbulent flow region and/or a central portion of the hollow body. Preferably the mesh is configured to provide minimum disruption to normal flow within the hollow body and through the perforated plate 5.

In the illustrated embodiment, the cradle is removable. This facilitates optional conversion of otherwise suitably configured shower heads to include this feature if required, or omitted if the feature is not needed. This is enabled by providing an extension collar 12 with seal 13 that can be inserted between a threaded head outlet opening 14 and the normal outlet plate assembly, which includes a plate retaining ring 15, perforated plate 5 and seal 16.

In other embodiments currently being developed, the additional collar 12 and seal 13 are not required and the mesh is integrally formed with the outlet assembly.

Extending from the inlet end of the hollow body 2 and inlet 3 is a handle portion 18, connected to an end cover 20 which includes a water-filter and a connecting spigot 19 for attachment to a hose connected to a suitable water supply (not shown). An adaptor inserted between spigot and hose (not shown) may also be provided to enable connection to a different type of hose if required.

The design of the handle itself and the angle of inclination relative to the outlet plate 5 are preferably selected to be ergonomic and enable comfortable extended use by an operator.

Figure 4:
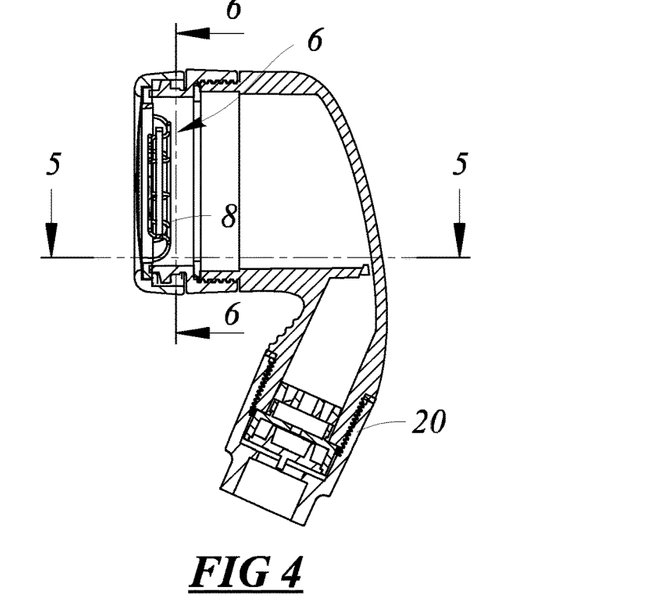
FIG. 4 is a cross sectional view of the shower head taken on line 4-4 of FIG. 3.
Figure 5:
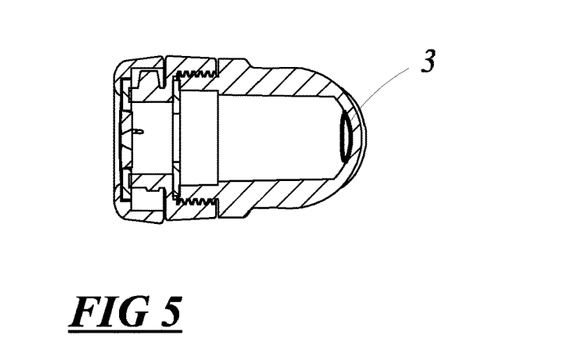
FIG. 5 is a cross sectional part view of the shower head taken on line 5-5 of FIG. 4 illustrating the cross sectional shape of the water inlet to the hollow body.
Figure 6:
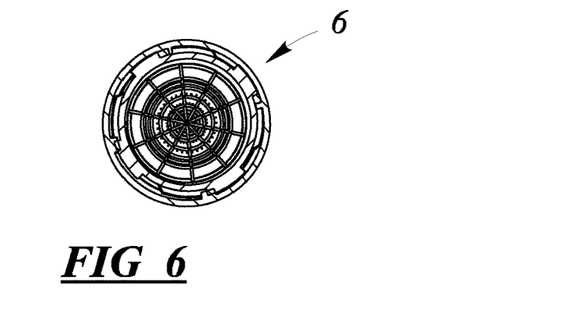
FIG. 6 is a sectional view taken on line 6-6 of FIG. 4.
Figure 7:
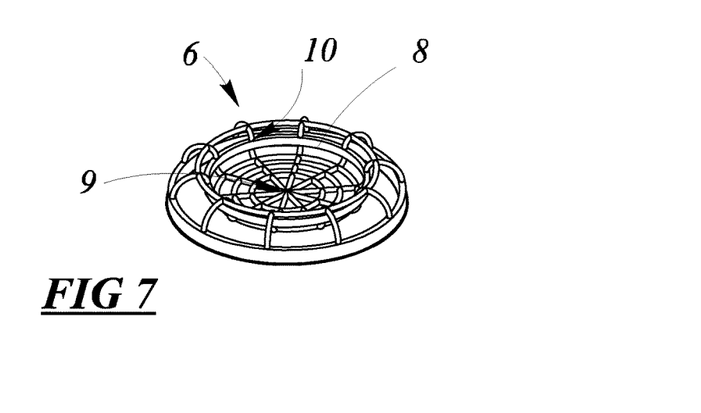
FIG. 7 is an enlarged perspective view of the mesh formation shown in the previous figures.
Figure 9:
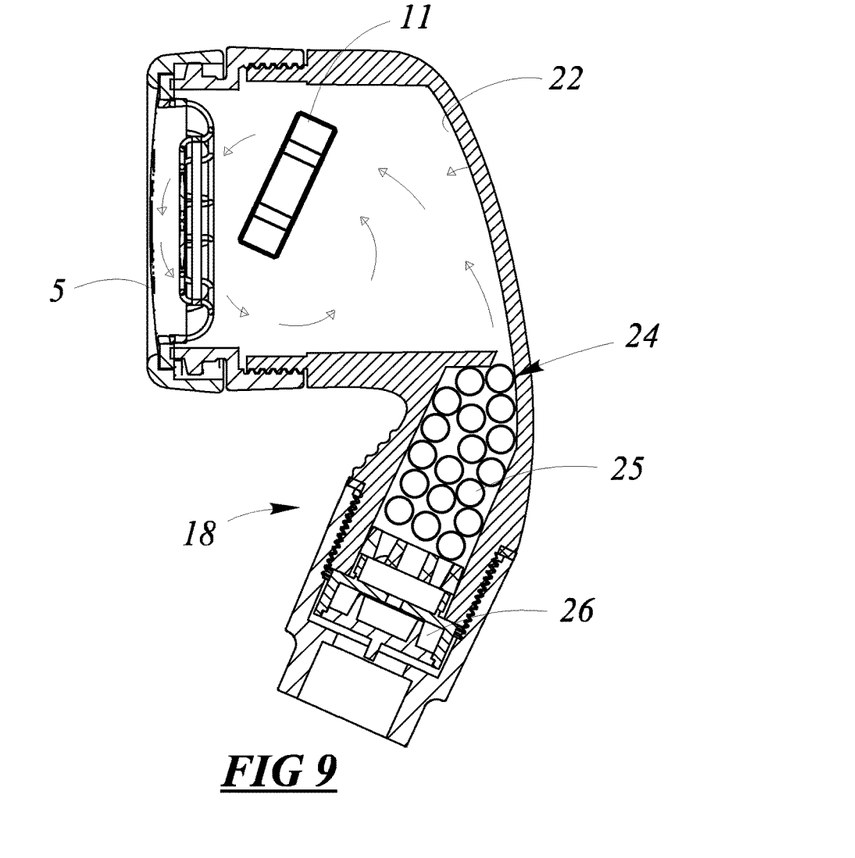
FIG. 9 is an enlarged cross sectional view of the shower head as shown in FIG. 4 annotated to show water flow and tablet movement within the shower head during use.

In addition to the handle design, the hollow body is also carefully configured to achieve turbulent flow within the body. In one particularly preferred form as illustrated in FIGS. 4, 5 and 9, the inlet 3 has a generally slit like configuration which exits closely adjacent a rear wall 22 of the hollow body which is inclined slightly toward the perforated plate 5. This causes the water flow to curve toward the plate. As the apertures in the plate are quite small, not all the water can freely exit, and as a result a turbulent generally circulating flow pattern is induced as illustrated in FIG. 9.

Desirably, the shower head also includes means to pre-treat the water flow before it enters the hollow body. In one preferred form as illustrated, this is achieved by provision of aeration pre-treatment chamber 24 disposed upstream of the inlet to the hollow body. In one embodiment, treatment and/or aeration is achieved by captively locating particulate matter in the pre-treatment chamber, whereby passage of water through this chamber around the particulate matter causes air bubbles of air to be created which pass through with the water into the hollow body. Air may also be entrained into the hollow body through the perforated plate, which is preferably slightly concave when viewed from outside the device.

Preferably, the particulate matter is in the form of beads 25 as shown in FIG. 9. More preferably, the particulate matter comprises a material that also interacts with the water to enhance its properties by, for example, ionising the water. Suitable bead materials include Tourmaline, Silver, Cerussite, Vitamin C, Vitamin D and products such as Million Guard™ produced by Koa Glass Company and which is an antimicrobial glass powder with Silver ions retained in the glass network structure that are gradually released.

Desirably the shower head is configured such that in use the water is entering the hollow body from an upper region thereby creating a waterfall-like stream which in turn enhances the Lenard effect by colliding with the lower wetted surfaces in the hollow body to produce negative ions. Such ions may already be present as the water collides with the wetted particulate matter in the pre-treatment chamber, where this is included.

Preferably the shower head also includes means for filtering out unwanted impurities such as chlorine or the like. This may be part of, or separate to, the means for generating negative ions.

Additional fine mesh filters 26 may also be included in the shower head, preferably within the handle as illustrated in FIG. 9.

Preferably, the shower head and disintigratable tablets are configured such that during use with a warm water supply at typical pressure and hair washing temperature, the tablets take around 2 to 4 minutes to disintegrate and provide a flow of water dispersed treatment to a user. Examples of typical water inlet pressure to the shower heads include a pressure range 50-200 KPa, temperature range of 10-40 degrees Celcius, preferably 25-32 degrees Celcius and outlet flow rate of 4-12 litres per minute, preferably 5-8 litres per minute as may be controlled by a flow regulator. However, it will be appreciated that the apparatus and tablets can be configured to work under different operating conditions if required.

In one preferred form, the shower head is configured to function as an increased pressure reduced water usage shower head.

In one preferred form, the increased pressure and reduced water usage is achieved at least in part by use of a perforated plate having a thickness range of 0.2 to 0.35 millimetres and perforations of a preferably round shape, 0.02 to 0.03 millimetres in diameter, with a total of between approximately 300 and 500 perforations and more preferably about 400 perforations. Preferably, the pattern of perforations is arranged to be concentrated around a central region of the perforated plate and do not extend to the circumferentially outer portion of the plate to provide a focused spray pattern whereby the water (with or without treatment) can be carefully directed to regions of the head undergoing treatment and reduce the risk of the spray extending beyond the treatment basin. Preferably the inlet to the hollow body is small so as to increase the pressure of the water entering the hollow body. In one preferred form the inlet is in the form of a slit opening with a maximum length of around 10-14 mm and maximum width of about 2-3 mm. The same principle is applied to other openings such as the inlet to the pre-treatment chamber and the perforations in the plate.

Figure 1:
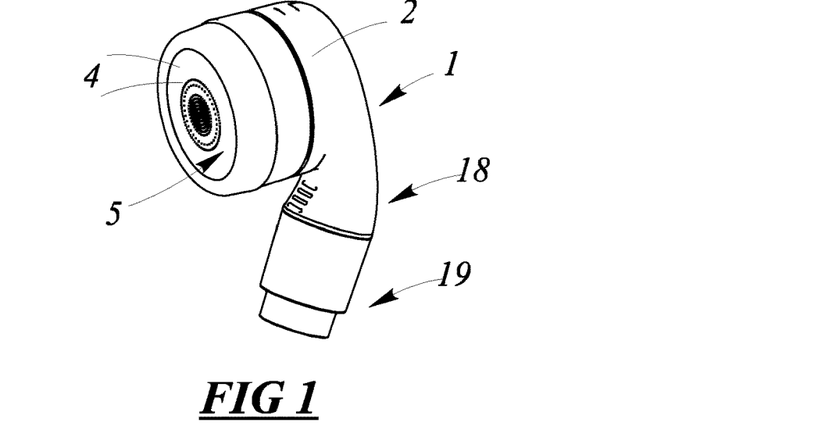
FIG. 1 is a perspective view of a first embodiment hand held shower head according to the first aspect of the invention.
Figure 2:
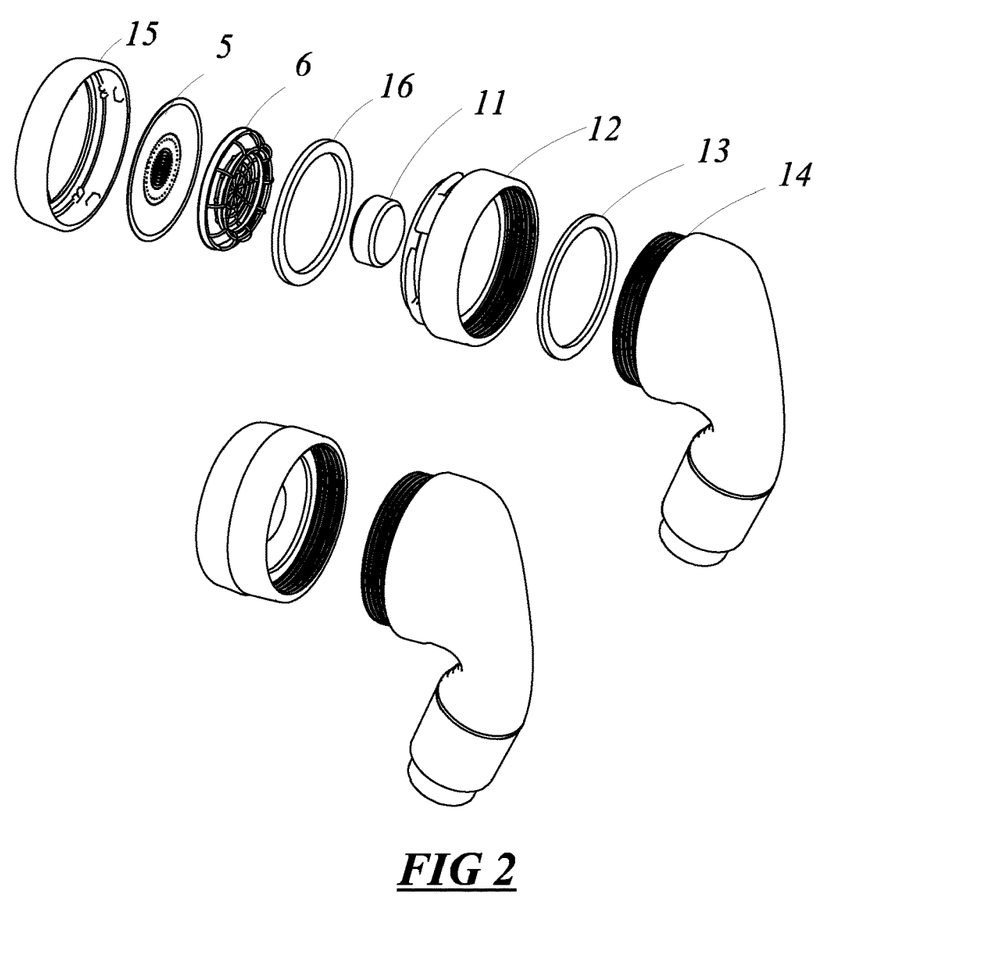
FIG. 2 is an exploded view of the components of the shower head shown in FIG. 1.
Figure 3:
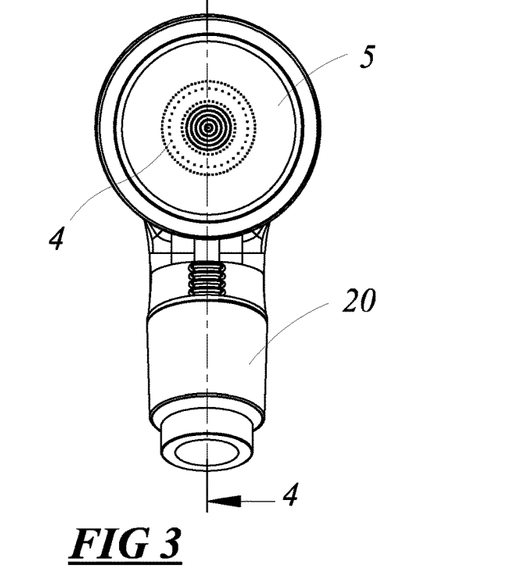
FIG. 3 is a front view of the shower head of the previous Figures with a hose adaptor.

Preferably, the disintegratable tablets have a shape which will be readily conveyed by the turbulent flow within the hollow body of the shower head 1, such that in use the tablet is caught up in the flow and repeatedly impacted against the mesh formation 6 so as to cause gradual disintegration of the tablet into the exiting water flow. One example of a suitable shape is shown in FIG. 2. In this regard it has been found that incorporation of one generally flat major surface can assist with ensuring the tablet is readily conveyed within the turbulent flow.

Figure 10:
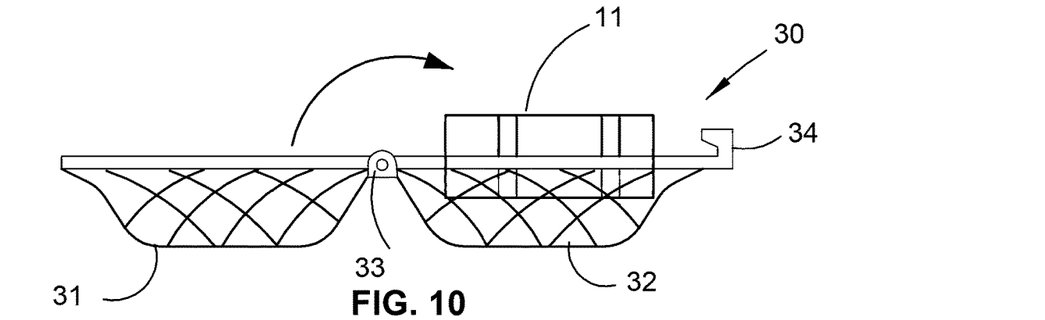
FIG. 10 is a side view of a mesh pod in an open configuration with a water disintegratable tablet.
Figure 11:
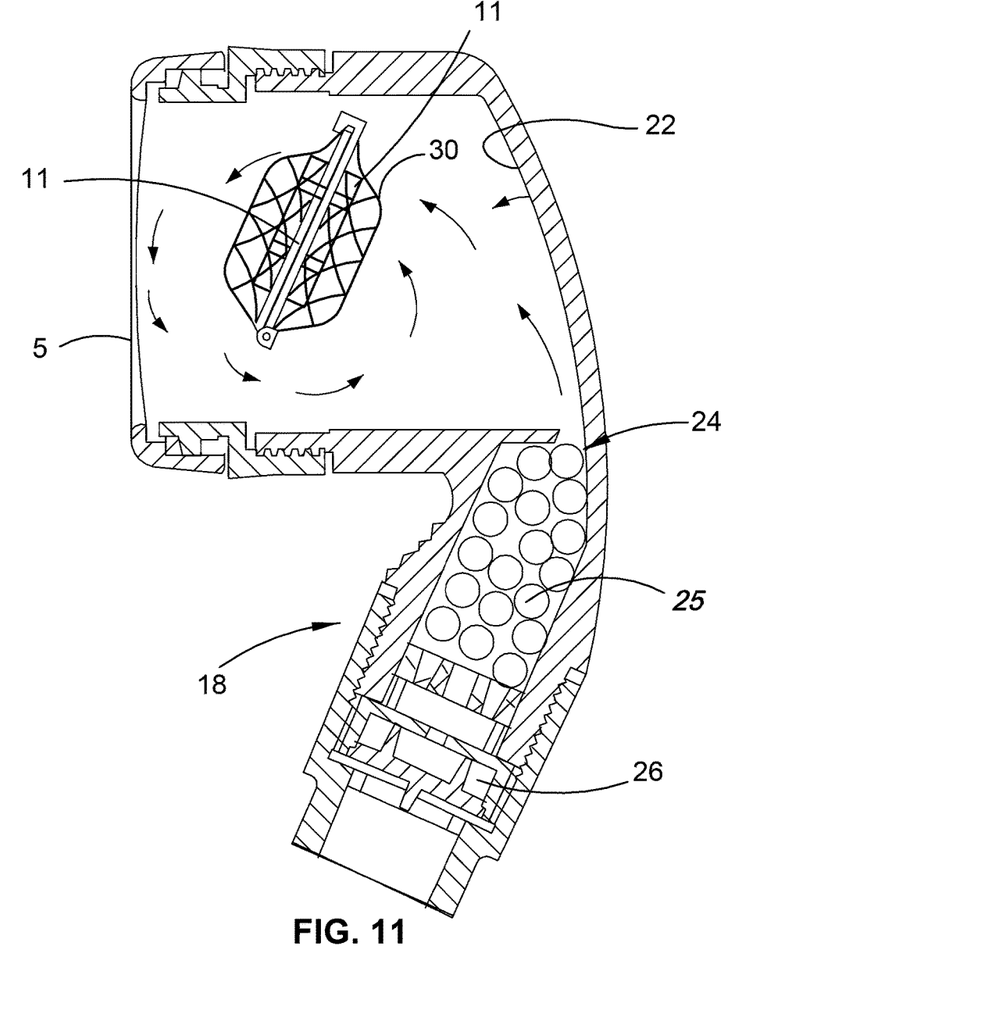
FIG. 11 is an enlarged cross sectional view of the shower head as modified for use with the mesh pod of FIG. 10 as shown.

In another form of the invention, such as that shown in FIGS. 10 and 11, the mesh may be designed to encapsulate the tablet in a similar manner to a tea strainer to utilise a mesh pod 30, whereby the entire mesh pod moves within the turbulent flow, and the tablet moves within the mesh pod in an abrading manner and is thereby dispersed into the water flow exiting the perforated plate. The mesh pod can be of any suitable shape as long as it can be opened to receive treatment tablets as required. In the example shown in FIG. 10 the pod includes two half formations 31 and 32 which are hingedly connected at 33 and closeable via a catch 34.

Figure 8A:
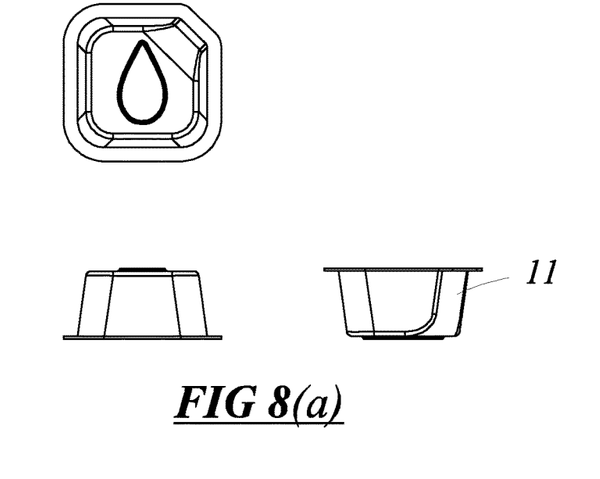
FIGS. 8(a) and 8(b) indicate further samples of preferred shapes of wax style (wrapped) treatment tablets and compressed powder (unwrapped) treatment tablets for use in the shower head of the previous Figures.
Figure 8B:
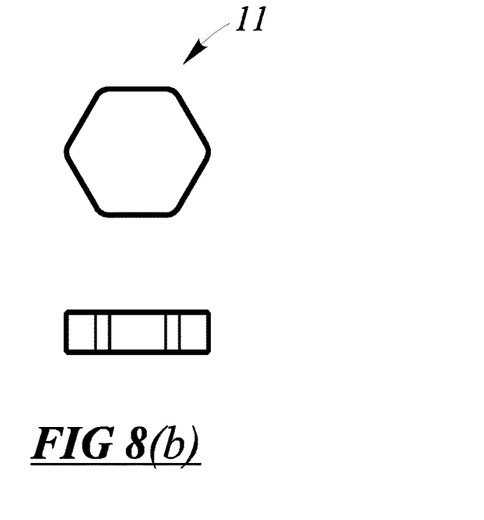

In a preferred hair treatment system according to the invention, the tablets include a cleanser and a range of treatment tablets. In one range, the cleansing tablet is in a compressed powder form and the treatment tablets are in a wax like form. An example of one preferred shape for a wax-like deep treatment or conditioning tablet is shown in FIG. 8(a) in a capsule style package, and an example of a compressed powder cleansing tablet (unwrapped) is shown in FIG. 8(b). It would be understood that the use of the wax-like treatment tablets of the present invention are preferred for hair treatments, though such tablets have a tendency to soften against the perforated exit screen, blocking the holes. However, the mesh formation of the shower apparatus of the present invention operates to enable use of this form of tablet as it prevents the blockage from occurring.

Examples of suitable formulations for the cleansing and treatment tablets are set out below, together with details of recommended treatment procedures using the shower head and tablets of the invention.

A preferred embodiment of a cleansing tablet for use in the showerhead apparatus of the present invention comprises about 20% (w/w) peppermint essential oil, about 27% (w/w) alky polyethylene glycol ether, about 25% (w/w) sodium cocoyl isethionate, about 3.5% (w/w) polyvinylpyrrolidone and about 25% buffered salts.

Another preferred embodiment of a cleansing tablet for use in the showerhead apparatus of the present invention comprises about 8% (w/w) peppermint essential oil, about 5% (w/w) sodium lauryl sulphacetate, about 60% (w/w) sodium cocoyl isethionate, about 12.5% (w/w) saponins, about 0.5% (w/w) microcrystalline cellulose, about 5% (w/w) calcium stearate and about 5% (w/w) citric acid.

A preferred embodiment of a strengthening treatment tablet for use in the showerhead apparatus of the present invention comprises about 3% (w/w) Emulgade® 1000NI, about 29% (w/w) PEG-4000, about 7% (w/w) cetiol-C5, about 5% (w/w) Tween-80, about 4.5% (w/w) cetrimonium chloride, about 1% (w/w) TERIC® N9, about 5% (w/w) hydrogenated castor oil, about 1.3% (w/w) phenoxyethanol, about 6% (w/w) TERIC® BL8, about 4% (w/w) TERIC® N5, and about 20% (w/w) plant oil, wherein the tablets comprises about 8% (w/w) argan oil.

Another preferred embodiment of a strengthening treatment tablet for use in the showerhead apparatus of the present invention comprises about 4% (w/w) Emulgade® 1000NI, about 43% (w/w) PEG-4000, about 7% (w/w) cetiol-C5, about 6% (w/w) TERIC® 16A30, about 7.5% (w/w) cetrimonium chloride, about 0.5% (w/w) TERIC® N9, about 2% (w/w) hydrogenated castor oil, about 1.0% (w/w) phenoxyethanol, about 1% (w/w) soy bean protein extract and about 16% (w/w) plant oil, wherein the tablets comprises about 2% (w/w) argan oil and/or marula oil.

A preferred embodiment of a colour care tablet for use in the showerhead apparatus of the present invention comprises about 5.5% (w/w) Emulgade® 1000N1, about 34% (w/w) PEG-4000, about 8% (w/w) cetiol-C5, about 5.5% (w/w) cetrimonium chloride, about 1% (w/w) TERIC® N9, about 10% (w/w) hydrogenated castor oil, about 2.5% (w/w)

phenoxyethanol, about 5% (w/w) TERIC® N5, about 5% (w/w) ethylhexyl methoxycinnamate and about 15% (w/w) plant oil.

A further preferred embodiment of a colour care tablet for use in the showerhead apparatus of the present invention comprises about 5% (w/w) Emulgade® 1000NI, about 43% (w/w) PEG-4000, about 7% (w/w) cetiol-C5, about 6% (w/w) TERIC® 16A30, about 7.5% (w/w) cetrimonium chloride, about 0.5% (w/w) TERIC® N9, about 2% (w/w) hydrogenated castor oil, about 1.0% (w/w) phenoxyethanol, about 2% (w/w) ethylhexyl methoxycinnamate, and about 15% (w/w) plant oil.

A preferred embodiment of a hydration tablet for use in the showerhead apparatus of the present invention comprises about 4% (w/w) Emulgade® 1000NI, about 40% (w/w) PEG-4000, about 4% (w/w) cetiol-C5, about 6% (w/w) cetrimonium chloride, about 1% (w/w) TERIC® N9, about 11% (w/w) hydrogenated castor oil, about 2.5% (w/w) phenoxyethanol, about 6% (w/w) TERIC® N5 and about 16% (w/w) plant oil.

Another preferred embodiment of a hydration tablet for use in the showerhead apparatus of the present invention comprises about 5% (w/w) Emulgade® 1000NI, about 43% (w/w) PEG-4000, about 8% (w/w) cetiol-C5, about 6% (w/w) TERIC® 16A30, about 7.5% (w/w) cetrimonium chloride, about 0.5% (w/w) TERIC® N9, about 2% (w/w) hydrogenated castor oil, about 1.0% (w/w) phenoxyethanol, and about 16% (w/w) plant oil.

A preferred embodiment of a treatment spray for use after cleaning and/or treating the hair using one or more tablets of the present invention with the showerhead apparatus of the present invention comprises about 1.5% (w/w) Tween-20, about 12.5% (w/w) cetrimonium chloride, about 0.5% (w/w) phenoxyethanol, about 10% (w/w) cationic silicone emulsion and water.

A preferred embodiment of a cream spray for use after cleaning and/or treating the hair using one or more tablets of the present invention with the showerhead apparatus of the present invention comprises about 4% (w/w) centrimonium chloride, about 3.5% (w/w) glyceryl stearate citrate, 2% (w/w) sodium cocoyl isethionate, about 3% (w/w) hydrogenated castor oil, about 10% (w/w) cetiol C5, and 6% plant oil.

A preferred embodiment of a finishing spray for use after cleaning and/or treating the hair using one or more tablets of the present invention with the showerhead apparatus of the present invention comprises 4% (w/w) plant oil, 85% (w/w) cyclopentasiloxane, 2% (w/w) ethylhexyl methoxycinnamate, 1% (w/w) phenoxyethanol and 8% (w/w) cetiol C5.

Method of Hair Treatment

In a preferred embodiment of the present invention, there is also provided a method of hair treatment comprising the steps of:

rinsing the hair with the shower apparatus comprising a cleansing tablet for approximately 2-3 minutes; and/or rinsing the hair with the shower apparatus comprising a treatment tablet for approximately 2-3 minutes; and optionally spraying the hair with about 3-6 mls of the treatment spray, cream spray or finishing after cleaning and/or treatment.

Although the invention has been described with reference to specific examples it will be appreciated by those skilled in the art that the invention may be embodied in many other forms.

The invention claimed is:

1. A shower head configured to deliver a continuous dose of water dispersed treatment from a water disintegratable tablet form treatment source, the shower head including:

a hollow shower head body having a restricted water inlet opening at one region and a water outlet at another region, the water outlet being defined by perforations in a perforated plate, and a perforate mesh formation, defined by a matrix of rigid elements against which a disintegratable tablet form treatment source can abrade, disposed within the hollow shower head body between the water inlet opening and the perforated plate, wherein the restricted water inlet opening is configured to deliver water into the hollow shower head body in a plane which is parallel to and spaced from the perforated plate, and the hollow shower head body is shaped to direct at least a portion of that water flow from the restricted water inlet downwardly toward the perforated plate, such that creates, in use, a rotating turbulent water flow within the hollow shower head body which at least in part circles within the hollow shower head body tangentially to the perforated plate, prior to the water exiting through the perforated plate, wherein a water disintegratable solid tablet form treatment source introduced into the hollow shower head body between the water inlet opening and the mesh formation prior to use is caused to rotate and move within the rotating, turbulent water flow so as to be agitated by the rotating turbulent water flow against the mesh formation and repeatedly abrade against the mesh formation to assist in the disintegration of the water disintegratable tablet and thereby be dispersed into the rotating, turbulent water flow prior to the water exiting the hollow shower head body through the perforated plate.

2. The shower head of claim 1, wherein the mesh formation is a fixed mesh formation and is disposed adjacent, but spaced from, the perforated plate.

3. The shower head of claim 2, wherein the fixed mesh formation is configured to define a bowl like cradle portion, having a flat base region and sloping sides, opening away from the perforated plate.

4. The shower head of claim 3 wherein the shower head and water disintegratable tablets used therein are configured such that during use with a warm water supply at typical pressure and hair washing temperature, the water disintegrable tablets take around 2 to 4 minutes to disintegrate and provide a flow of water dispersed treatment to a user.

5. The shower head of claim 1, wherein the mesh formation is configured to encapsulate the water disintegrable tablet to form a pod, whereby the entire mesh pod moves within the turbulent flow, and the water disintegrable tablet moves within the mesh pod in an abrading manner and is thereby dispersed into the pressurized, rotating, turbulent water flow prior to the water exiting the hollow shower head body through the perforated plate.

6. The shower head of claim 1, further comprising an aeration pre-treatment chamber disposed upstream of the inlet of the hollow unobstructed shower head body.

7. The shower head of claim 6, wherein the perforated plate is configured to entrain air into the hollow unobstructed shower head body.

8. A shower head of claim 1 wherein the restricted water inlet has a cross section that has a maximum length of 10-14 mm and maximum width of 2-3 mm.

\* \* \* \* \*